(12) United States Patent
Ayad

(10) Patent No.: US 6,916,294 B2
(45) Date of Patent: Jul. 12, 2005

(54) BRAIN RETRACTION SENSOR

(75) Inventor: Michael Ayad, Washington, DC (US)

(73) Assignee: George Washington University, Washington, DC (US)

( * ) Notice: Subject to any disclaimer, the term of this patent is extended or adjusted under 35 U.S.C. 154(b) by 340 days.

(21) Appl. No.: 10/190,638

(22) Filed: Jul. 9, 2002

(65) Prior Publication Data

US 2004/0010208 A1 Jan. 15, 2004

(51) Int. Cl.7 .......................... A61B 5/103; A61B 5/117
(52) U.S. Cl. ....................................................... 600/587
(58) Field of Search ............................... 600/547, 587, 600/372, 300, 544

(56) References Cited

U.S. PATENT DOCUMENTS

| | | |
|---|---|---|
| 3,888,117 A | 6/1975 | Lewis |
| 3,958,562 A | 5/1976 | Hakim et al. |
| 4,147,161 A | 4/1979 | Ikebe et al. |
| 4,263,900 A | 4/1981 | Nicholson |
| 4,317,452 A | 3/1982 | Russo et al. |
| 4,735,208 A | 4/1988 | Wyler et al. |
| 4,784,150 A | 11/1988 | Voorhies et al. |
| 4,869,255 A | 9/1989 | Putz |
| 4,903,702 A | 2/1990 | Putz |
| 4,945,896 A | 8/1990 | Gade |
| 5,112,347 A | 5/1992 | Taheri |
| 5,201,325 A | 4/1993 | McEwen et al. |
| 5,207,227 A | 5/1993 | Powers |
| 5,247,932 A | 9/1993 | Chung et al. |
| 5,377,675 A | 1/1995 | Ruskewicz et al. |
| 5,551,439 A | 9/1996 | Hickey |
| 5,769,781 A | 6/1998 | Chappuis |
| 5,807,270 A * | 9/1998 | Williams ............... 600/547 |
| 5,876,577 A | 3/1999 | McAleer et al. |
| 5,916,171 A | 6/1999 | Mayevsky |
| 6,022,770 A | 2/2000 | Hook et al. |
| 6,061,593 A | 5/2000 | Fischell et al. |
| 6,093,145 A | 7/2000 | Vom Berg et al. |
| 6,104,941 A | 8/2000 | Huey et al. |
| 6,144,866 A | 11/2000 | Miesel et al. |
| 6,296,615 B1 | 10/2001 | Brockway et al. |

OTHER PUBLICATIONS

Hongo et al., "Monitoring retraction pressure on the Brain", J. Neurosurg., vol. 66, Feb., 1987, pp. 270–275.

Donaghy et al, "Pressure Measurement beneath Retractors for Protection of Delicate Tissues", American Journal of Surgery (1972) 123:429–431.

Andrews et al., "A Review of the Brain Retraction and Recommendations for Minimizing Intraoperative Brain Injury", Neurosurgery, vol. 22, No. 6, Dec. 1993, pp. 1052–1063.

(Continued)

Primary Examiner—Max F. Hindenburg
Assistant Examiner—Brian Szmal
(74) Attorney, Agent, or Firm—Gray, Cary, Ware & Freidenrich LLP

(57) ABSTRACT

An electrode grid device is disclosed comprising a deformable envelope, further comprising non-polarizable electrodes and a pressure recording port. The device is designed to allow for monitoring of brain retraction pressure and local cortical electrical activity including DC potential, as well as to redistribute the force applied during retraction and thereby diminish the chance of focal brain injury during surgery. Retraction pressure recorded is equal over the full area of contact, providing a more meaningful measurement than simply at one point on the retractor. A means is disclosed for evacuation of air from the system to improve accuracy and fidelity of the pressure measurements. It is a further aspect of the device to allow for measurement of intracranial pressure, DC potential and EEG in epileptic and severe head trauma patients for management of edema and injury, respectively.

43 Claims, 14 Drawing Sheets

OTHER PUBLICATIONS

Piper et al., "The Camino Intracranial Sensor: Is It Optimal Technology? An Internal Audit With A Review of Current Intracranial Pressure Monitoring Technologies", Neurosurgery, (2001), 49:1158–65.

Behrens et al., "Subdural and depth electrodos in the presurgical evaluation of epilepsy", Acta Neurochi (1994), 128:84–87.

Rosenorn, J, "Self–Retaining Brain Retractor Pressure During Intracranial Procedures", Acta Neurochirurgica, (1987), 85:17–22.

Sakaki et al., "Possible Control of Intermittent Cerebral Ischemia by Monitoring of Direct–Current Potentials", J. Neurosurg, (2001) 95:495–9.

Ayad, M., "Electrocortical Concomitants of Neuroprotection and Ischemic Damage Following Cerebral Circulatory Arrest" Doctoral Dissertation, (1994).

Jackson et al., "Technical report: A silicone rubber suction drain for drainage of subdural hematomas", Surgery, Oct. 1971, vol. 70, No. 4. pp 578–579.

Palatinsky et al., "SSEP and BAEP Monitoring of Temporary Clip Application and Induced Hypotension during Cerebrovascular Surgery" in Intraoperative Monitoring Techniques in Neurosurgery, (C.M. Loftus et al., eds.), 1994, Cpt. 7, pp. 61–71, McGraw–Hill, Inc., NY.

Rampil I.J., "Electroencephlogram" in Textbook of Neuroanesthesia with Neurosurgical and Neuroscience Perspectives, (M.S. Albin, ed.), 1996, Cpt. 6, pp. 193, 207–208, McGraw–Hill, Inc., NY.

* cited by examiner

BRAIN RETRACTION SENSOR

FIELD OF THE INVENTION

This invention is related generally to intracranial sensors for prevention of retractor blade injury (i.e., "retraction injury") of the brain, and subdural monitoring devices.

BACKGROUND

A retractor is an instrument used during surgery for, among other things, holding back structures adjacent to the immediate operative field (See, e.g., U.S. Pat. No. 5,769, 781). During neurosurgical operations for aneurysms, tumors or other lesions located in the skull base, the surgeon must employ retracting devices in order to displace one or more lobes of the brain enough to gain adequate surgical exposure to the lesion. These retractors are adjusted by hand to optimize exposure. Unfortunately, it is very difficult for the surgeon to accurately gauge the amount of pressure actually applied to the brain during such placement of the retractor (see, e.g., Hongo et al., J Neurosurg 1987; 66:270–275). Moreover, it is also possible to inadvertently position the blade of the retractor such that a focal pressure point occurs at one particular area of the retractor blade pressing against the brain. Thus, injury to the brain can occur as a result of brain retraction when either the force applied is excessive or when the pressure is not adequately distributed to a large enough area of brain. This injury is thought to be the result of ischemia (inadequate blood flow) caused by the retraction, local trauma, or a combination of both.

It has been estimated that brain retraction injury occurs in approximately 10% of major cranial base tumor procedures and 5% of intracranial aneurysm surgeries (Andrews et al., Neurosurgery 1993; 33:1052–64). Various attempts have been made to develop technology to help minimize the incidence of this type of injury, with limited success. For example, a strain gauge or gauges attached to the retractor blade has been employed (Hongo et al., 1987; Rosenorn J., Acta Neurochir (Wein) 1987; 85:17–22). This approach has limited utility because pressure can only be measured from the point or points where the strain gauges are situated. As mentioned above, sometimes the brunt of the force occurs at the tip of the retractor blade where no strain gauge is present. Certainly this technique does little, if anything, to distribute force on the brain more evenly.

While knowing the amount of pressure applied will be helpful to the surgeon, the brain may be more or less sensitive to a given amount of pressure depending on its physiological state. The variables that influence the vulnerability of the brain to different degrees of retraction include the presence of subarachnoid hemorrhage (e.g., secondary to a ruptured aneurysm), depth of anesthesia, systemic parameters such as blood oxygen and carbon dioxide levels, and the particular region of the brain being retracted. As a result, electrophysiological monitoring of the brain can give a more accurate indication of when the threshold for injury is being approached. Intraoperative neurophysiological monitoring is commonplace during such operations, and typically the electroencephalogram (EEG) and somatosensory evoked potentials (SSEP) are employed. However, these modalities depend on the placement of electrodes on the scalp. Because of this, electrodes can only be placed to the extent that they do not interfere with the sterile surgical field, and obviously cannot be placed in the area of the craniotomy. Of course, this is precisely the part of the brain that needs to be monitored.

Thus, this type of recording from scalp leads can, at best, give information regarding regions of the brain adjacent to where the operation is occurring. Unfortunately, this method often reports erroneously favorable information that does not reflect the injury developing at the retractor site.

In neurosurgical operations where ischemia is anticipated (which includes most aneurysm procedures), high doses of anesthetics are typically administered to the patient to reduce cerebral metabolic rate and increase the tolerance of the brain to ischemia. Such high doses cause suppression of both the EEG and SSEP, thus rendering them ineffective for the detection of imminent brain injury. The recording of cortical direct current (DC) potentials from the brain is a technique that provides invaluable information about the functional status of the brain during situations of compromised blood flow (Ayad, doctoral dissertation© 1994; Sakaki et al., J Neurosurg 2001; 95:495–9). Further, DC potentials are not affected by anesthetic agents. This technique was utilized experimentally in the 1950's during operations for epilepsy. However, with the exception of the clinical study currently investigating the device described herein, the benefits of DC potential for monitoring brain injury intraoperatively have not been put to use. This is, no doubt, because a practical method for applying the electrodes to relevant parts of the brain without obscuring the operative field has not been available.

Measuring such DC potentials requires the placement of a non-polarizable electrode (e.g., platinum or Ag—AgCl rather than stainless steel) on the cortical surface. Stainless steel and other electrodes are unsatisfactory because ion deposition at the brain-electrode interface causes artifactual potentials which prevents registration of the true voltage signal. The cortical electrode is referenced against a non-polarizable electrode placed at a remote site from the brain, and a high-input impedance DC amplifier is used to record the voltage. An extracerebral site is essential for the reference electrode in order for it to remain "indifferent" to injurious processes that may be occurring in the brain. Depolarizations (i.e., negative potentials) of greater than 4–5 mV typically develop when the brain is subjected to ischemia or trauma. DC potential is ideal for assessing the status of a small, localized area of the brain without penetrating its surface. Further, conventional EEG and SSEP recordings from platinum electrodes produce less noise than stainless steel electrodes during ischemia.

Strips of silicone rubber containing Pt electrodes known as "subdural grids" are commonly placed on the brain underneath the dura mater of certain patients with epilepsy for long-term recording of EEG to localize areas of seizure activity prior to surgery (e.g., U.S. Pat. No. 4,735,208). Both materials, i.e., platinum and medical-grade silicone rubber, are biocompatible, and have been tolerated very well for periods of up to several weeks when used for this purpose (Behrens E, Zentner J, et al. Subdural and depth electrodes in the presurgical evaluation of epilepsy. Acta Neurochir 1994; 128:84–87). However, such devices do not allow for monitoring of intracranial pressure. This latter capability would be helpful because many epileptics who have implanted grids develop local brain swelling, and recognizing a pressure increase would allow appropriate management of edema. Additionally, such a device, which also monitors intracranial pressure, may allow for concurrent measurement of such pressure and EEG postoperatively from severe head trauma patients who have undergone surgery for the management of said trauma.

Currently, there is no technology available to record electrical activity from areas of the brain that are being retracted. Instead, areas remote to the retraction site are monitored, providing sub-optimal and sometimes misleading information about the status of the brain. Two prior patents (U.S. Pat. Nos. 4,784,150 and 4,945,896) have incorporated technology to monitor local cerebral blood flow and metabolic parameters, respectively, into a brain retractor blade. Neither are equipped with a means for monitoring retraction pressure. Moreover, for the reasons discussed previously, local electrocortical activity provides a more readily interpretable index, compared to these measures, of when the threshold for injury is being reached.

With respect to monitoring retraction pressure, devices have been manufactured commercially in the past to perform this, however none are readily available at present (e.g., Codman CPM-100 Brain Retraction Pressure Monitor [Codman & Shurtleff, Inc., Randolph, Mass.]; also see Hongo et al 1987). Furthermore, such devices require proprietary accessory equipment that is expensive, and they are cumbersome to use (Andrews et al., 1993). Other devices are attached to the arm of the retractor blade rather than to the blade (McEwen et al., U.S. Pat. No. 5,201,325), and only convey information about the point of greatest pressure. Even where the "pressure responsive" surgical tool assembly is attached to the retractor blade (e.g., Nicholson, U.S. Pat. No. 4,263,900 and Lewis, U.S. Pat. No. 3,888,117), such devices do not permit recording of electrical activity.

The Codman CPM-100 device and the retraction pressure monitor of Nicholson (see also Donaghy et al., Am J Surg 1972; 123:429–31) all differ from the sensor of the present invention in other important structural respects. Retraction pressure monitors of Codman, Nicholson and Donaghy et al. employ an expandable reservoir with internal electrodes (i.e., the electrodes do not contact the underlying tissue). Air or other fluid is pumped into or out of the reservoir depending on electrical contact, resulting in inflation or deflation of the reservoir. Since air is one of the fluids utilized, there is no means for eliminating air from the system. Physiological saline cannot be used, as it would short-circuit the electrodes. Further, air attenuates the fidelity and accuracy of hydraulic pressure monitoring systems.

In contrast, the device described herein utilizes a flexible but relatively non-expandable bladder that is completely liquid-filled and free of air prior to use. This serves as an efficient mechanism to evenly distribute applied force throughout the entire area of contact. Moreover, the presently disclosed device provides an accurate means for measuring retraction pressure without the need for a fluid pump or internal electrodes.

There have been attempts to fabricate brain retractor blades which more favorably distribute pressure, so as to lessen the chance of injury (Vom Berg, U.S. Pat. No. 6,093,145 and Borsody, U.S. Pat. App. No. 2002/0022770). Neither are capable of monitoring retraction pressure or any other sensing modalities.

A second utility of the present invention pertains to its intracranial placement at the time of surgery for the purpose of postoperative monitoring of intracranial pressure (ICP), as well as the modalities of electrical activity described previously (i.e., as a subdural sensor). This information will permit the neurosurgeon and critical care physician to optimally manage brain swelling and injury after surgery.

There are two types of operations in which use of the subdural sensor (SS) may be indicated. The first was mentioned above, i.e., patients with intractable epilepsy that is refractory to anticonvulsant medication may undergo placement of many subdural electrode grids in order to localize the focus identified by the EEG monitoring. Because the placement of many grids involves some manipulation of surface of the brain, sometimes patients can develop significant brain swelling which results in abnormally raised ICP. Occasionally ICP is raised to the point that alteration of mental status occurs, and this may only be identified as such after the patient undergoes a CT scan of the head. By having a monitor of ICP in these patients, elevations in ICP can be identified sooner, and treated promptly with mannitol or steroids.

The second type of operation in which subdural placement of the device may be helpful is for severe closed head injury. In cases of cerebral contusion, massive swelling of the brain often occurs and if not treated appropriately, can result in coma or death of the patient. When severe swelling has occurred or is anticipated, often these patients are taken to the operating room to undergo removal of the damaged portions of the brain in order to provide room for the swollen brain and reduce ICP. Virtually all of these patients have some type of ICP monitor placed at the time of surgery to permit assessment of the swelling postoperatively. Currently there are two types of ICP monitors used in this setting. The first is a ventriculostomy, which is an open-tipped catheter placed into the lateral ventricle of the brain and connected to a hydraulic transducer substantially similar to that used for the invention described. A ventriculostomy is advantageous because it permits not only measurement of pressure but also drainage of cerebrospinal fluid from the brain, which can aid in the lowering of ICP. However, after severe closed head injury, often the brain is so swollen that the ventricles are collapsed and placement of a ventriculostomy is impossible. The second type of ICP monitor currently available is an intraparenchymal probe which is placed into the substance of the brain through a small burr hole, and which records pressure from its tip by one of many methods (e.g., Camino fiberoptic monitor, Camino Laboratories, San Diego, Calif.). The disadvantages of this technique are that (1) it requires penetration of the brain with the probe, which itself causes a small amount of trauma, and (2) the pressure recorded from this type of probe is prone to non-trivial drift over a matter of days (Piper et al., Neurosurgery 2001; 49:1158–65). Furthermore, neither of these two types of ICP monitors permits the recording of local EEG or DC potential, which are valuable adjuncts in the assessment of brain injury. For these reasons, the present invention will be a superior monitoring device compared to the existing ICP monitors.

The tissue monitor described by Mayesvsky (U.S. Pat. No. 5,916,171) comprises a multiparametric apparatus able to monitor several modalities, including DC potential, ICP, a single channel of EEG, blood flow and NADH fluoremetry. Despite these aggregated modalities, there are a number of shortcomings. All parameters are recorded from the same, small area of cortex. Thus, all information will be reported from a small region that may not represent the bulk of the surrounding tissue, particularly, for example, if the area beneath the sensor is traumatized during placement, which might easily occur. Because it requires extensive, specialized equipment to operate, this system is clearly intended for use in a focused, research setting and not for routine monitoring of neurotrauma or epilepsy patients in the ICU.

As with a ventriculostomy, it should be noted that the pressure transducer utilized with the present device should be kept at the level of the distal end of the sensor (e.g; scalp incision) by the nursing staff in order to record an accurate pressure. Raising the transducer, due to the fluid column, will result in an artifactually low ICP and conversely, lowering the transducer below the appropriate level will cause an erroneously high ICP to be read. This aspect of the device can be readily managed by attentive staff, and is easily offset by the convenience, low cost, reliability and ubiquity of the standard hydraulic pressure monitoring apparatus in the intensive care unit and operating room.

Last, various procedures require postoperative evacuation of residual fluids, for example, following craniotomy (see Jackson et al., Surgery 1971; 70:578–9). In fact drainage of serosanguineous wound fluid or CSF from the subdural space often plays an important part in the postoperative managemant of patients with craniotomies, especially trauma. Typically, the placement of drainage devices (e.g., Jackson-Pratt drain, Allegiance Healthcare, McGaw Park, Ill.) is similar to that for subdural grids. Consequently, many of the patients who would be candidates for placement of the subdural sensor would ordinarily have J-P drains placed at the time of surgery. Thus, a subdural sensor comprising a means to drain residual fluids would be a useful device.

The present invention as disclosed provides the desired capabilities absent in the foregoing devices, in that it is designed to permit monitoring of brain retraction pressure or ICP, as well as local cortical electrical activity, including DC potential (i.e., via multiple electrode sites). It permits registration of equilibrated pressure over the full length of contact of the retractor blade. Further, the present device as disclosed allows for redistribution of the forces applied to the brain during retraction so as to diminish the chance of focal brain injury during surgery. For use postoperatively, the instant device provides a closed system for egress of serosanguineous fluid into a sterile, external collector.

SUMMARY OF THE INVENTION

A device is disclosed comprising an inextensible pressure distribution means (e.g., elastomer grid) that allows for redistribution of pressure along the surface of the brain when said device is in contact with said organ. It is an object of this invention that when the device is applied to a retractor blade, such distribution of pressure can reduce retractor injury. It is another object of this invention that the device can be applied subdurally for pre- and post-operative evaluation of epileptic and traumatic brain injury patients.

Further, the device comprises two ends, with a first elongated end comprising the distribution means, and a second end comprising an exit port. In a related aspect, the exit port engages the distribution means through the second end.

It is an object of this invention that the device comprises a plurality of electrodes exposed on an available surface, where the electrodes are spaced along the elongated first end of the device. Moreover, this electrode-exposed surface is adapted to contact the brain of a patient (e.g., a cortical electrode). In a related aspect, a non-electrode exposed surface comprises a sleeve or pocket which allows the device to be releasably coupled to a retractor blade or spatula. In a further related aspect, the electrodes are non-polarizable.

The device of the instant invention also comprises a non-polarizable needle electrode, which allows for referencing of the cortical electrode at a remote site. In addition, electric and hydraulic conduits engage the pressure distribution means through the exit port available at the second end of the device.

The device of the present invention is envisaged to be a thin, substantially flat article comprising a biocompatible substrate, which is sufficiently elastically deformable, such that it may conform to the contours of variously shaped angles. In a related aspect, said contours comprise the surface of the brain and/or the inner surface of the cranium. In a further related aspect, the angles are present on the surface of a retractor blade or spatula.

It is another object of this invention that the electric conduit, which engages the distribution means via the exit port, further comprises a tail, where the tail allows for communication between the instant device and peripherals, such as EEG apparatus or DC amplifier. In a related aspect, the tail may comprise a plug for such communication.

It is another object of this invention that the hydraulic conduit, which engages the distribution means via the exit port, further comprises at least two lumenal surfaces to allow for fluid ingress to and egress from the distribution means. In a related aspect, said conduit allows for the evacuation of air bubbles from the distribution means. In a related aspect, the conduit comprises a double lumen catheter. In a further related aspect, such a catheter may engage separate fluid flow connectors for each lumen, such as female luer-lock connectors. Moreover, such connectors are envisaged to be housed in a single unit.

It is an object of this device, when applied subdurally, that egress of subdural wound fluid may be directed through a third lumen of said conduit into an external collection device, such as a bag. In a related aspect, the fluid is allowed to flow into such an external collection device by gravity flow.

The device of the present invention is envisaged to comprise a cavity filled with a physiologically inert fluid such as saline. In a related aspect, the cavity should accommodate sufficient pressure so as not to appreciably expand the distribution means.

It is an object of this invention that hydraulic pressure, equilibrated throughout the distribution means, can be recorded from the catheter by a standard strain gauge apparatus used in the clinical setting. This equilibrated pressure represents brain retraction pressure when the device is situated between the brain and retractor blade. When situated in the subdural space, the equilibrated pressure reflects ICP. For example, see method as disclosed in Ikebe et al. (U.S. Pat. No. 4,147,161).

It is an object of the present device to comprise a process of redistribution of the forces applied to the brain during retraction so as to diminish the chance of focal brain injury during surgery. Further, the process further comprises monitoring of brain retraction pressure and local cortical electrical activity, including but not limited to DC potential, EEG and evoked potentials. In a related aspect, the surgeon practicing such monitoring adjusts retraction based on abnormal readings correlating with retraction pressure and cortical electrical activity. In a further related aspect, such abnormal recordings include but are not limited to, loss of EEG fast activity accompanied by slow waves, burst suppression EEG patterns, EEG suppression, suppression of evoked potential amplitude, evoked potential latency delay or negative DC potential shift. For example, when the negative DC potential shift is >3 mV, this would be considered an abnormal reading.

It is an object of the present device to comprise a process of concurrent measurement of intracranial pressure and local electrical activity (previous paragraph) postoperatively from severe head trauma patients who have undergone surgery for the management of said trauma.

It is a further object of the present device to comprise a process of monitoring epileptics who have implanted grids to determine the degree of local brain swelling for appropriate management of edema.

These and other important objects will be apparent from the descriptions of the instant invention which follow.

DETAILED DESCRIPTION OF THE INVENTION

Definitions

Figure 1:
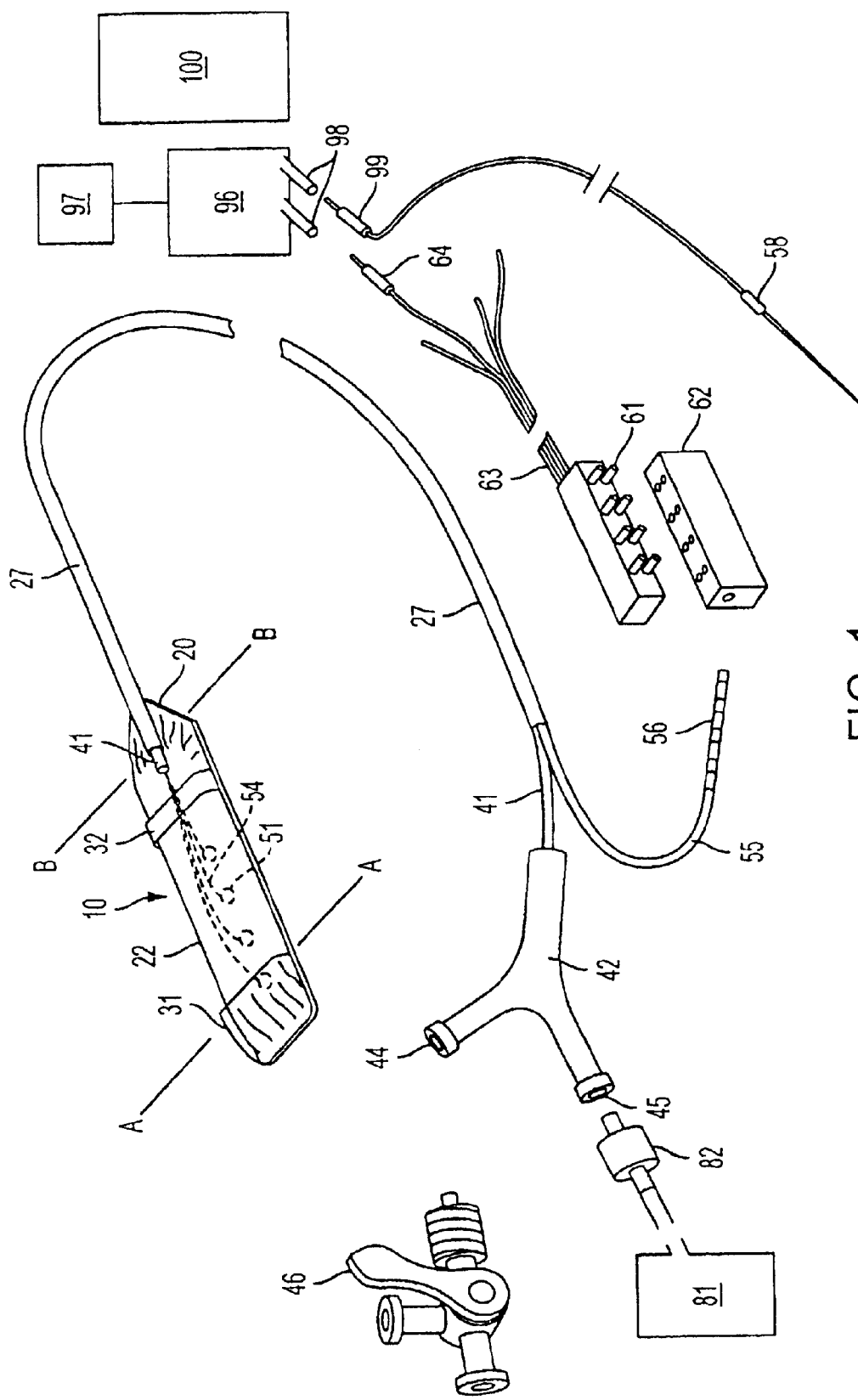
FIG. 1 Enlarged perspective view of preferred embodiment of brain retraction sensor (BRS) including proximal ends of electrode tail and double-lumen catheter. Also illustrated is a proprietary EEG cable assembly and connection (via stopcock) to hydraulic pressure recording apparatus.

As used herein "subdural", including grammatical variations thereof, means situated underneath the dura mater and overlying the pia mater or arachnoid membrane of the brain.

As used herein "sensor", including grammatical variations thereof, means a device designed to respond to physical stimuli such as, but not limited to, electrical, temperature, blood flow, or partial pressure of oxygen or carbon dioxide, and transmit resulting impulses for interpretation, recording, movement or operating control.

As used herein "substantially inextensible cavity", including grammatical variations thereof, means a fixed or defined limit of expansion of an unfilled space within a mass. In a one embodiment, the cavity has a capacity of expansion of between about 5% and about 10% volume change from pre-filled resting state (i.e., liquid filled without force applied) per 100 mm Hg change in pressure. In another embodiment, the cavity has a capacity of expansion to include but not limited to about 6%, 7%, 8% or 9% volume change from pre-filled resting state per 100 mm Hg change in pressure. In a related aspect, the cavity would occupy a confined space of between about 0.1 mm$^3$ and about 0.8 mm$^3$ in the liquid-filled, expanded state. In a further related aspect, the cavity would occupy a confined space of, but not limited to, about 0.2 mm$^3$, 0.3 mm$^3$, 0.4 mm$^3$, 0.5 mm$^3$, 0.6 mm$^3$ or 0.7 mm$^3$ in the liquid filled, expanded state.

In another related aspect, a distribution means or elastomer grid comprising the first elongated end contains an unfilled space which includes but is not limited to a cavity, bladder, sinus, dilation, hollow or interconnected lumen, wherein the surfaces of such distribution means are minimally elastically deformable, essentially allowing for a low amount of variation in volume, and where such means remains substantially flat when such space is filled.

As used herein "cistern", including grammatical variations thereof, means a reservoir for liquids.

As used herein "configured", including grammatical variations thereof, means designed to fit a particular space. In a preferred embodiment, the dimensions of the instant device are such that length and width of the distribution means are between about 5 cm to about 8 cm (length) and about 2 cm to about 3 cm (width), respectively. In a related aspect, the length is contemplated to be about 6 cm or 7 cm and the width is contemplated to be about 2.1 cm, 2.2 cm, 2.4 cm, 2.5 cm, 2.6 cm, 2.7 cm, 2.8 cm, or 2.9 cm. In a further related aspect in, the subdural sensor the length of the distribution means is between about 13 cm to about 15 cm, including the drain tip.

As used herein "substantially flat" or "relatively thin", including grammatical variations thereof, relate to a range of thickness of the BRS/SS devices corresponding to be between about 1 mm and about 4 mm. In a preferred embodiment, the thickness of the instant device is between about 1 mm to about 1.5 mm in the collapsed state and between about 2.5 mm to about 4.0 mm in the fully expanded state. In a related aspect, the thickness of the device is about 1.1 mm, 1.2 mm, 1.3 mm or 1.4 mm in the collapsed state, and about 2.6 mm, 2.7 mm, 2.8 mm, 2.9 mm, 3.0 mm, 2.1 mm, 3.2 mm 3.3 mm, 3.4 mm, 3.5 mm, 3.6 mm, 3.7 mm, 3.8 mm or 3.9 mm in the fully expanded state.

As used herein "labyrinthine network", including grammatical variations thereof, means an array of elements (to include but not limited cavities, bladders, sinuses, dilations, hollows or interconnected lumens) combined to form an substantially inextensible cistern within the distribution means of the instant BRS/SS.

As used herein "matrix", including grammatical variations thereof, means material in which something is enclosed or embedded.

As used herein "fluid-flow directing connectors", including grammatical variations thereof, means a coupling which guides the route of fluid movement.

As used herein "conduit", including grammatical variations thereof, means a natural or artificial channel through which something is conveyed. In a preferred embodiment, that which is conveyed is a fluid. In a more preferred embodiment, the fluid is a physiologically inert liquid, such as saline.

As used herein "releasable coupling", including grammatical variation thereof, means a fastener, link or connector that is able to be set free from restraint or confinement of a separate surface.

As used herein "elastically deformable', including grammatical variations thereof, means an ability to become misshapen or to change size or shape while being able to recover size and shape after said change.

As used herein "bio-compatible", including grammatical variations thereof, means adaptability with living tissue or a living system by not being toxic or injurious and not causing immunological rejection. In a related aspect, bio-compatible materials include, but are not limited to, silicone-based materials, thermoplastic elastomers, low density polyethylene, polyurethane and other thermoplastic materials.

As used herein "noncompliant", including grammatical variations thereof, means unyielding to condition, treatment or operation. For example, a tube composed of stainless steel or hard plastic would be considered noncompliant.

As used herein "residual fluid", including grammatical variations thereof, means bodily fluids left behind after surgery or injury to the brain. For example, serosanguineous fluid.

As used herein "lumen", including grammatical variations thereof, means the cavity or bore of a tube.

As used herein "surface", including grammatical variations thereof, means the superficial aspect of something. For example, the superficial aspect of a cavity would be considered a surface.

As used herein "atraumatic", including grammatical variations thereof, means without injury to living tissue, where such injury would typically be caused by an external agent.

As used herein "liquid" and "fluid", including grammatical variations thereof, are used interchangeably. Further, the terms mean a substance having neither the qualities of a solid or a gas.

As used herein "hydraulic", including grammatical variations thereof, means operated, moved, or effected by means of water or other liquid in motion.

As used herein, "physiologically inert", including grammatical variations thereof, means a substance that does not affect a characteristic appropriate to normal organism functioning, wherein said substance lacks a chemical or biological effect.

As used herein "burr hole" means a perforation in the calvarium made by a surgeon for the purpose of placing a drain or other device, or for facilitating removal of a bone flap. The diameter of a typical burr hole is between about 1 cm and 1.5 cm.

As used herein "perforation", including grammatical variations thereof, means a hole made by or as if by piercing or boring.

As used herein "gravity flow", including grammatical variations thereof, means the movement of a material that is neither a gas or a solid by the attraction of the mass of the earth.

DC amplifier as used herein means an amplifier with input impedance $>10^{12}$ $\Omega$, has an infinite time constant, which may be battery powered, but not so limited, and permits measurement of voltage potential between active and reference inputs, allowing amplification of signal for recording on a monitor.

Embodiments

The present invention envisages a device comprising a substantially inextensible, pressure distribution means contained within a mass. The mass comprises a thin, elastically deformable, biocompatible composition. In a preferred embodiment, such a device, for example, is envisages to include a cavity which has a fixed or defined limit of expansion within said mass. Such a cavity may be actualized by a membranous sac or bladder. Alternatively, it may be actualized by a labyrinthine network of tubes or interconnected chambers within a matrix of compressible material where the totality of lumenal volume is continuous with two exit ports.

In a related aspect, such a device allows for redistribution of pressure along the surface of an organ when said device is in contact with said organ. In a preferred embodiment, the device is placed in contact with a brain. In a more preferred embodiment, the brain is a human brain.

The device of the present invention is envisaged to measure physiological responses, including but not limited to EEG, intracranial pressure, DC potential and evoked potentials. Other physiological responses which may be measured by the invention include but are not limited to local cerebral blood flow (e.g. Powers, U.S. Pat. No. 5,207,227) and oxygen partial pressure (e.g. McAleer et al., U.S. Pat. No. 5,876,577; also, Miesel et al., U.S. Pat. No. 6,144,866). In a preferred embodiment, the device of the present invention concurrently measures physiological responses and focal pressure exerted on the brain when releasably coupled to a tool which produces such focal pressure. In a related aspect, said tool includes, but is not limited to a brain retractor.

In a preferred embodiment, the brain retraction sensor (BRS) described herein incorporates a subdural electrode grid and a double-lumen plastic catheter into a thin, silicone rubber envelope which can be filled with sterile saline through the catheter. The second port of the catheter allows air bubbles to be evacuated from the silicone 'bladder'. In a preferred embodiment, a sleeve made of silicone rubber on the side opposite the Pt electrodes permits the device to be slipped on the end of a brain retractor blade. Once the bladder is filled with saline, a stopcock on the secondary port is closed and the primary port is connected to a conventional pressure-recording setup in the operating room, as is commonly used for measuring arterial or central venous blood pressure. In another preferred embodiment, calibration of the device is carried out with the sensor held at the level of the brain region to be retracted. In a related aspect, a proprietary cable is attached to the 'tail' of the grid assemble so that each of the four platinum electrodes can be individually connected to input leads of a recording monitor (e.g., see Putz, U.S. Pat. No. 4,869,255). In a further related aspect, a separate platinum needle electrode is inserted by the surgeon into temporalis, or other exposed muscle, so as to provide a reference for measuring DC potential.

In a preferred embodiment, when the surgeon is prepared to begin brain retraction, the retractor blade (attached to a flexible steel arm) is positioned on the brain as it normally would be placed. The BRS is, thus, situated between the brain and the retractor blade, with the electrodes contacting the portion of the brain being retracted. In a related aspect, the saline-filled bladder distributes the applied retraction pressure equally over the whole surface of the sensor, thereby eliminating focal pressure points prone to cause injury. In a further related aspect, because the pressure within and along the sensor is equal, the measurement of retraction pressure transduced through the catheter is a more meaningful representation than merely pressure at only one particular point, since pressure may vary considerably along the retractor blade if no bladder is present.

In a preferred embodiment, important information, supplemental to retraction pressure is obtained by recording DC potential and EEG from each of the four platinum contacts. When deemed necessary, this information can be conveyed to the surgeon by the person monitoring the parameters, so that adjustments can be made in the retractor positioning and injury to the brain can be avoided.

As stated above, the present invention is also directed to intracranial placement of a subdural sensor at the time of surgery for the purpose of postoperative monitoring of intracranial pressure (ICP), thus, permitting the neurosurgeon and critical care physician to optimally manage brain swelling and injury after surgery. For example, in one embodiment, at the conclusion of surgery, the sensor is placed underneath the dura mater on the surface of the brain. Typically the bone flap (i.e., piece of calvarium removed during the operation) has 2 or more burr holes approximately ½" in diameter along its perimeter which facilitate the craniotomy at the beginning of the procedure. Thus, at the conclusion of the case, when the bone flap is replaced, the plastic catheter and electrode-tail of the sensor can be allowed to exit the skull via one of the burr holes and then exit the scalp through a small puncture site in the skin.

The technique for placement of the instant device described above (i.e., intracranial placement) is identical to that of a subdural Jackson-Pratt drain (Allegiance Healthcare, McGaw Park, Ill.) for postoperative evacuation of residual fluid following craniotomy (see Jackson et al., Surgery (1971) 70:578–9). As stated earlier, i.e., those who would be candidates for placement of the subdural sensor. Therefore, in another embodiment, the subdural sensor incorporates a drain (comparable to a J-P) into the distal end and catheter of the device in order to permit egress of subdural fluid into an external collection bag. In a similar fashion to J-P, the instant device can easily be removed at the bedside of a patient after placement whenever its use in no longer required (i.e., without requiring additional surgery).

DETAILED DESCRIPTION OF THE PREFERRED EMBODIMENTS

FIG. 1 illustrates a perspective view of a Brain Retractor Sensor (BRS) 10, representing various parts comprising a fully assembled device, including cross-sectional planes A and B.

The BRS 10, includes an elongated elastomer grid 20 comprising projections 31 and 32 from the back face of said grid 20, where said projections extend away from the grid 20 such that the grid 20 can be releasably coupled to a retractor blade (not shown).

The grid 20 further includes a number of flat platinum electrode disks 51 partially exposed and coplanar with the elastomer grid 20 on the tissue engaging, front face of grid 20, through which such electrodes make contact with said tissue. Also, internal to the grid 20 are lead wires 54, one wire 54 attached to each electrode 51. Lead wires 54, each of which has its own thin layer of insulation (e.g., but not limited to, Teflon®), come together and engage at one end of the grid 20 where they separately enter a conduit 27.

In the embodiment illustrated in FIG. 1, the grid 20 further includes a substantially inextensible cavity or bladder, the roof of which is at 22. This grid 20 may comprise silicone-based materials, thermoplastic elastomers, low-density polyethylene, polyurethane and other thermoplastic materials. In a preferred embodiment, the grid comprises Silastic®, a biocompatible, silicone rubber material available from Dow Corning.

The cavity or bladder meets at one end of the grid 20 and engages the conduit 27, where said conduit comprises one end of a hydraulic double lumen catheter 41, which engages said bladder at one end of grid 20, and one end of a separate electrical conduit 55, which engages the lead wires 54 at the same end of grid 20. The hydraulic double lumen catheter 41 allows for ingress and egress of fluids into and out of the bladder/cavity. The electrical conduit allows for communication of electrophysiological information between the contacted tissue and external apparatus (e.g., EEG monitor).

A second end of the hydraulic double lumen catheter 41 engages a housing 42 containing twin hydraulic connecting ports 44 and 45 (e.g., luer-locks), where one connecting port is separately attached to one lumen comprising the hydraulic double lumen 41.

Further, one of the twin hydraulic connectors 44 is used for the evacuation of air bubbles in the hydraulic conduit 41 through the stopcock 46. Moreover, the other member of the twin connectors 45 (i.e., for connecting to hydraulic pressure recording apparatus) is connected to a strain gauge apparatus 81 via a male luer-lock connector 82. Said gauge apparatus 81 comprises a conventional output display, monitor and suitable power source.

A second end of the electrical conduit 55 comprises a contact/connector for external apparatus such as an EEG device, where the tail comprises a cable assembly 56. The contacts on the cable assembly 56 engage the EEG cable assembly connecting block 62, where the block engages connecting wires 63 (which includes male EEG input pin jack 64) of the EEG cable assembly via connecting pins 61. Further, said input pin jack 64 electrically connects to a conventional EEG, where said EEG comprises a conventional output display, monitor and suitable power source.

At least one of the connecting wires 63 of the EEG cable assembly electrically connects to a DC amplifier 96 at electrical connection 98. A platinum needle electrode 58 also electrically connects to the DC amplifier 96. Said DC amplifier 96 comprises a conventional output display, monitor and suitable power source. Moreover, at least one of the connecting wires 63 of the EEG cable assembly electrically may connect to a separate external apparatus 100, wherein apparatus 100 comprises a conventional output display, monitor and suitable power source.

Such a set up allows for real-time monitoring of electrophysiological responses of the brain during retraction procedures.

Figure 2A:
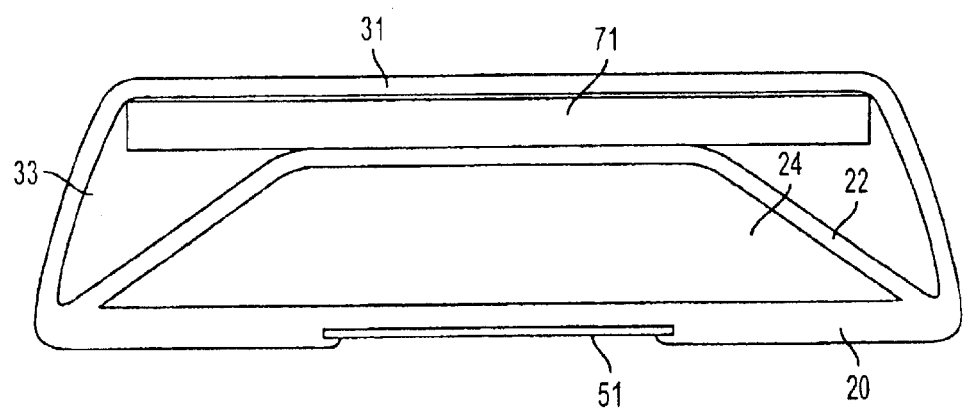
FIG. 2A Cross-sectional view of preferred embodiment of BRS at point A from FIG. 1 with retractor blade in pocket.

In FIG. 2A, a cross-sectional view of the BRS 10 is illustrated from the perspective from point A of FIG. 1.

A detailed view of the fluid-filled (expanded) bladder/cavity 24 is shown in FIG. 2A, including the roof 22 and the bladder/cavity 24 of the elastomer grid 20. Further, a partially exposed electrode 51 which makes contact with the tissue (i.e., the brain) is also shown.

Releasable-coupling is demonstrated in the cross-sectional view of FIG. 2A via engagement of the shell of the distal pocket 31 with the retractor blade tip 71. As seen in the figure, the blade 71 lies within the cavity 33 comprising the distal pocket shell 31.

Figure 2B:
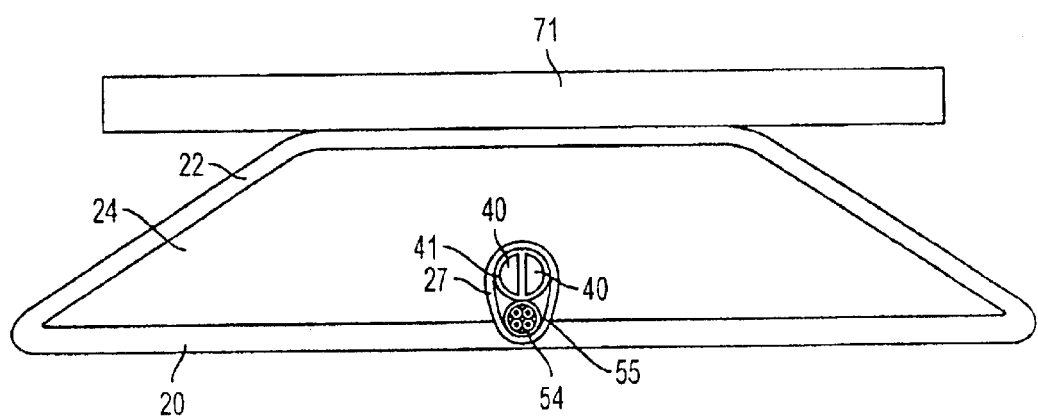
FIG. 2B Cross-sectional view of BRS at point B from FIG. 2.

In FIG. 2B, the cross-sectional view of the BRS 10 is illustrated from the perspective from point B of FIG. 1.

A detailed view of the fluid-filled (expanded) bladder/cavity 24 is shown in FIG. 2B, including the roof 22 and bladder/cavity 24 of the elastomer grid 20, as well as the retractor blade 71. Further, a cross-section of conduit 27, which sheathes the hydraulic double lumen catheter 41 and electrical conduit 55, is also shown.

Cross-sectional detail of the sheathing-conduit 27 illustrates the inner lumenal surfaces 40 of the double lumen catheter 41 and the electrical conduit 55, including the coated wire leads 54. The lumens each serve separate purposes; i.e., one lumen is for the evacuation of gases such that there are no air bubbles present in the conduit and cavity/bladder, and the other lumen to measure/monitor pressure.

Figure 3:
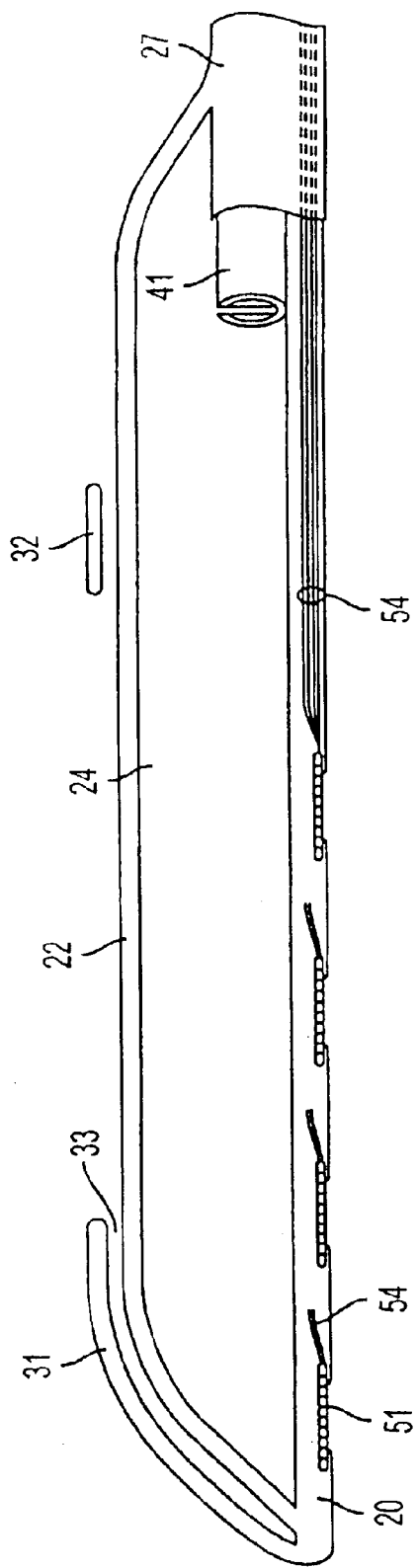
FIG. 3 Longitudinal section view of BRS at a point just adjacent to midline.

In FIG. 3, a longitudinal-section view just adjacent to the midline of the expanded BRS 10 is illustrated. This view shows four partially exposed electrodes 51, including their associated lead wires 54 coming together and engaging at one end of the grid 20. Further, the figure shows one end of the double lumen catheter 41 engaging the bladder/cavity 24. As both the lead wires 54 and double lumen catheter 41 extend away from the grid 20, they are sheathed in conduit 27.

FIG. 3 also shows the roof 22 of said cavity/bladder 24 and both projections allowing for releasable-coupling to a retractor blade (i.e., 31 and 32), including a separate cavity 33 available under the shell of the distal pocket 31.

Figure 4:
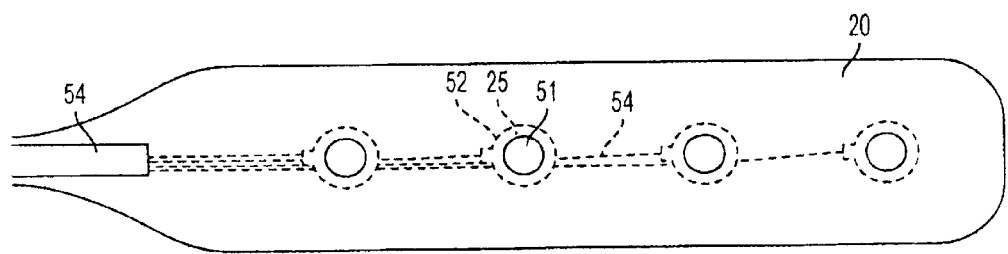
FIG. 4 Plane view of bottom (contact surface) of either BRS or subdural sensor (SS).

FIG. 4 illustrates a plane view of the bottom (tissue contact surface) of a retractor or subdural device.

The figure shows in detail four partially exposed electrodes 51, including a thin rim of Silastic® 25 in the bladder floor of the grid 20 overlying the outer margin of the Pt electrode 51 at 52, where the thin outer rim of Silastic® 25 holds the electrodes 51 in the grid 20. Further, as shown in the figure, each electrode 51 engages a separate coated lead wire 54 come together at one end of the grid 20 at electrical conduit 55.

Figure 5:
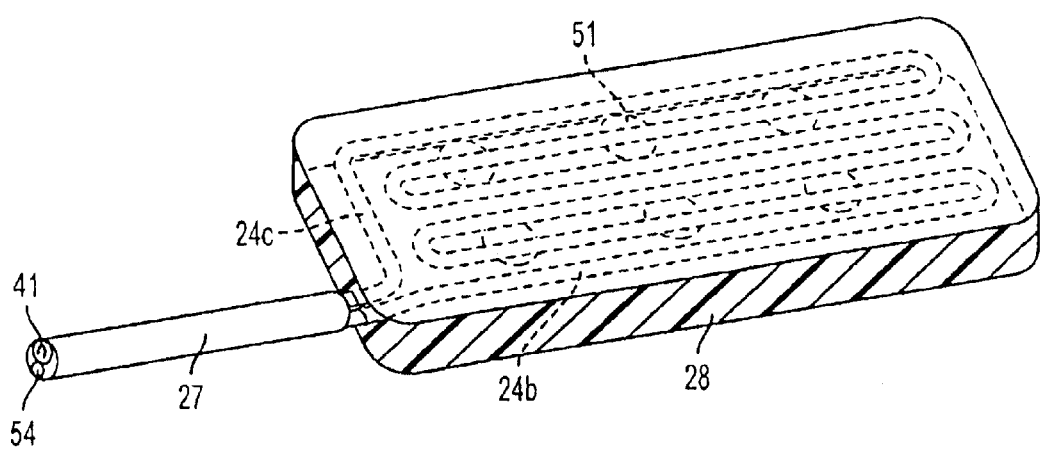
FIG. 5 Perspective view of alternative embodiment of distribution means for either BRS or intracranial sensor illustrating labyrinthine network of interconnected lumens continuous with both inlets of double-lumen conduit (lead wires not shown).

FIG. 5 is a perspective view of an alternate embodiment of the distribution means for either retractor application or subdural (intracranial) application.

In FIG. 5 the distribution means is illustrated by a series of interconnected lumens 24b and 24c. Each end of each lumen 24b and 24c is separately engaged to only one lumen of the double lumen catheter 41. Also shown are the electrodes 51 and the sheathing conduit 27, where the conduit 27 comprises the coated wire leads 54. Further, the figure also shows a compressible matrix cushion 28 which houses the lumens 24b and 24c, as well as the electrodes 51 and wire leads 54 (not shown within matrix).

Figure 6:
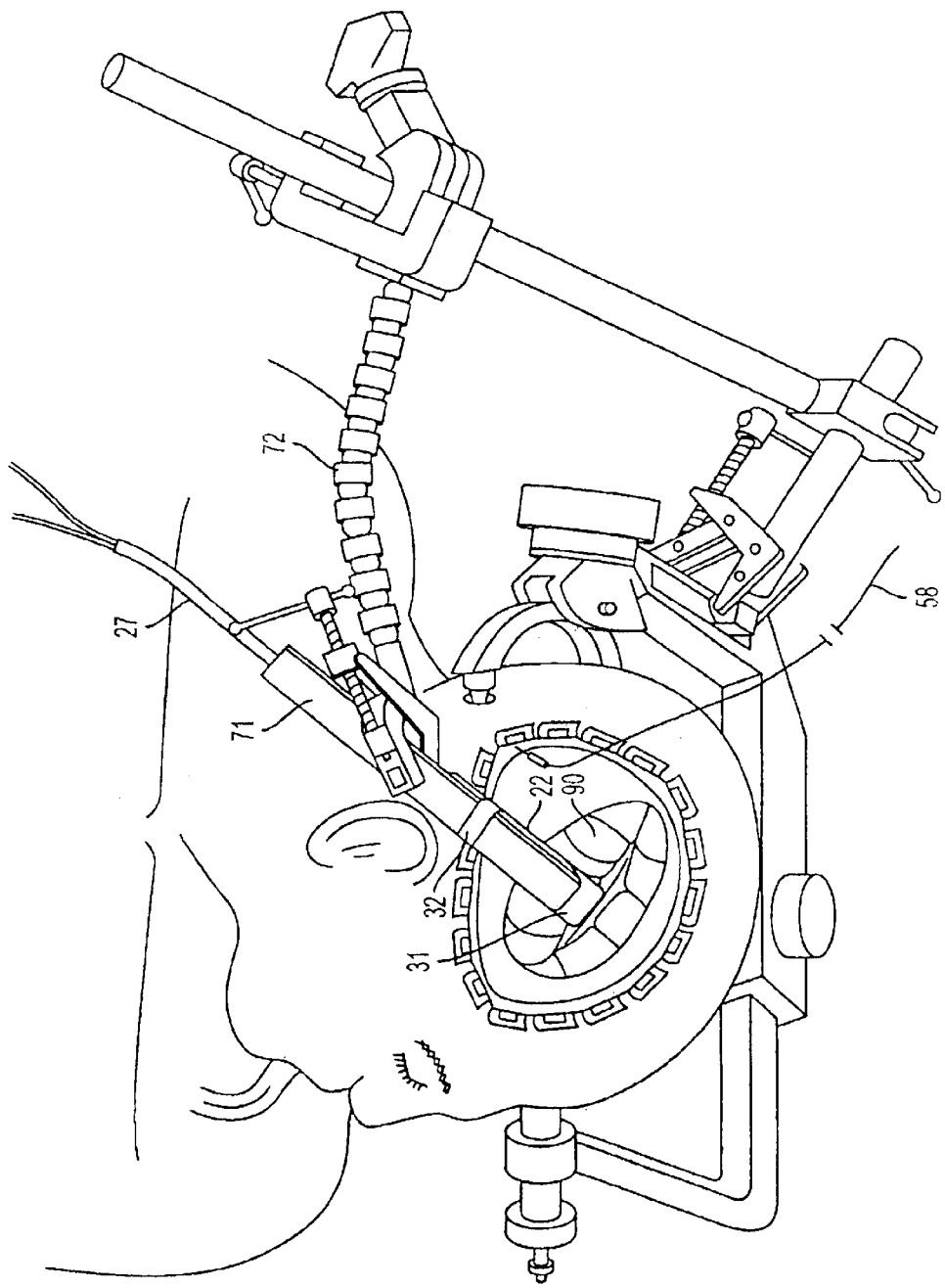
FIG. 6 Perspective view of BRS in use with a Greenberg retraction assembly for neurosurgical operation requiring retraction of patient's right temporal lobe.

FIG. 6 is a perspective view of the BRS 10 in use with a Greenberg retraction assembly 72 during retraction of a patient's right temporal lobe 90, includes a platinum needle reference electrode with male EEG input pin jack on distal end 58. The figure also shows a malleable metal brain retractor blade 71 with BRS 10 engaged, where the BRS 10 has exposed the roof of the cavity/bladder 22, the shell of the distal pocket 31 and the proximal sleeve 32. Further, the sheathing conduit 27 is also shown.

Figure 7:
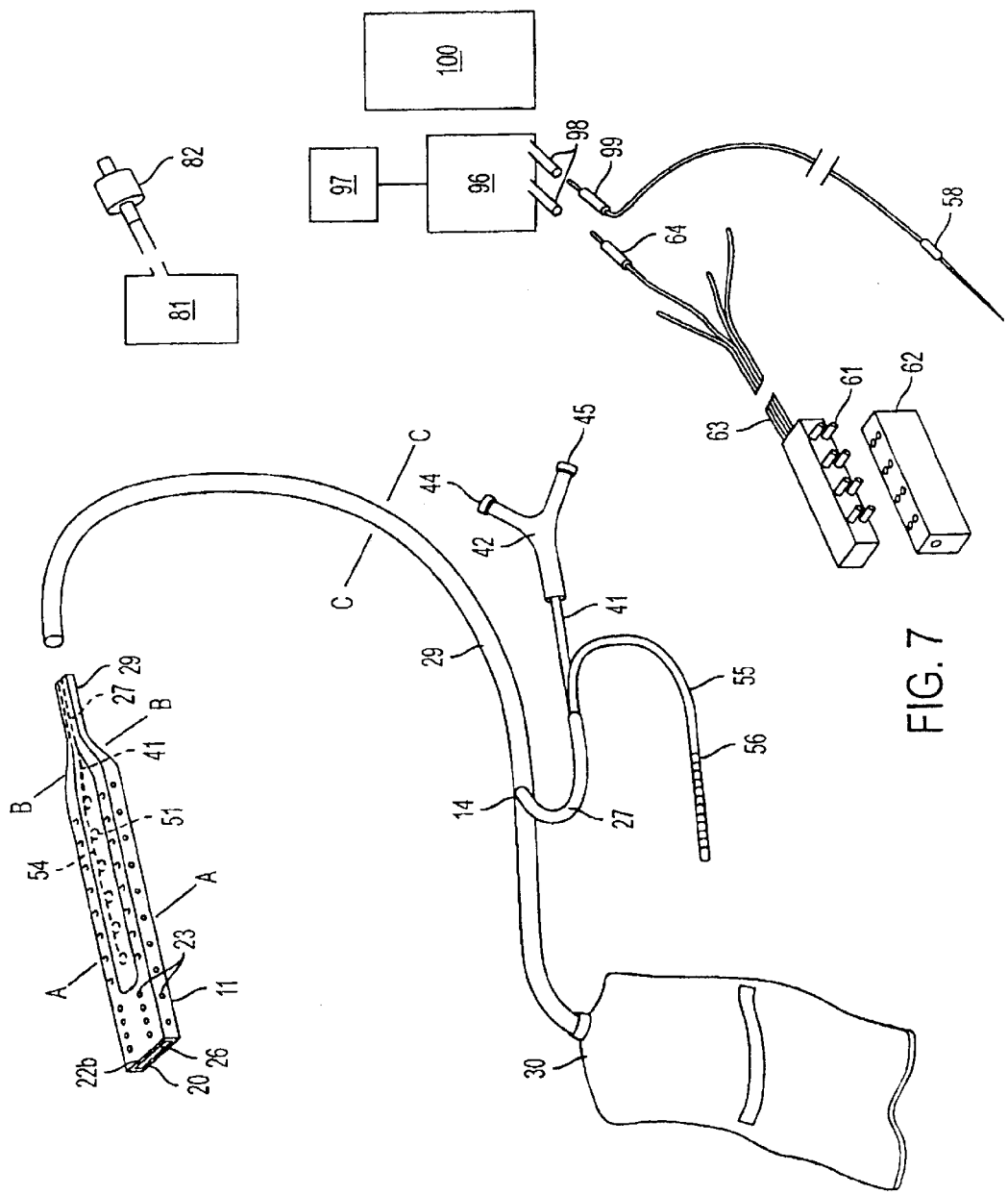
FIG. 7 Perspective view of a preferred embodiment of the subdural sensor illustrating the perforated drain incorporated into the sensor. The exiting conduit includes a solid drainage tube, double-lumen catheter with luer-lock ports, and the electrode tail.

FIG. 7 illustrates a perspective view of a Subdural Sensor (SS) 11, representing various parts comprising a fully assembled device, including cross-sectional planes A, B and C.

The SS 11, includes an elongated elastomer grid 20. The grid 20 comprises a number of flat platinum electrode disks 51 partially exposed and coplanar with the elastomer grid 20 on the tissue engaging, front face of grid 20, through which such electrodes make contact with said tissue. Also, internal to the grid 20 are lead wires 54, one wire 54 attached to each electrode 51. Lead wires 54, each of which has its own thin layer of insulation (e.g., but not limited to, Teflon®), come together and engage at one end of the grid 20 where they enter a conduit 27. Moreover, conduit 27 is sheathed within the lumen of a second conduit 29.

In the embodiment illustrated in FIG. 7, the grid 20 further includes a subdural drain, the holes 23 of which are exposed on the outer surface of the grid 20, and where the roof of the drain is at 22b. Further, the grid 20 comprises a substantially inextensible cavity or bladder, where the roof of the cavity/bladder is continuous with roof 22b. The grid 20 may comprise silicone-based materials, thermoplastic elastomers, low-density polyethylene, polyurethane and other thermoplastic materials. In a preferred embodiment, the grid comprises Silastic®, a biocompatible, silicone rubber material available from Dow Corning.

The subdural sensor also comprises a lumen 26, where the lumen 26 serves to evacuate residual fluids such as, for example, serosanguineous wound fluid or CSF. Such fluids collect in the lumen 26 and flow by gravity to a fluid collection bag 30 via the sheathing conduit 29. Further, said sheathing conduit 29 comprises a sealed exit point 14 for emergence of the conduit 27 from the sheathing conduit 29. Moreover, said exit point 14 may be sealed by any means known in the art (e.g., but not limited to, a gasket), such that residual fluid collected from the lumen 26 of the subdural drain does not leak from said exit port 14.

The cavity or bladder meets at one end of the grid 20 and engages the conduit 27. Conduit 27 further comprises one end of a hydraulic double lumen catheter 41, where said catheter 41 engages said bladder at the same one end of grid 20. Moreover, one end of a separate electrical conduit 55, which comprises the lead wires 54, engages at the same end of grid 20. The hydraulic double lumen catheter 41 allows for ingress and egress of fluids into and out of the bladder/cavity and pressure monitoring. The electrical conduit allows for communication of electrophysiological information between the contacted tissue and external apparatus (e.g., EEG monitor).

A second end of the hydraulic double lumen catheter 41 engages a housing 42 containing twin hydraulic connecting ports 44 and 45 (e.g., luer-locks), where one connecting port is separately attached to one lumen comprising the hydraulic double lumen 41.

Further, one of the twin hydraulic connectors 44 is used for the evacuation of air bubbles in the hydraulic conduit 41 through the stopcock 46. Moreover, the other member of the twin connectors 45 (i.e., for connecting to hydraulic pressure recording apparatus) is connected to a strain gauge apparatus 81 via a male luer-lock connector 82. Said gauge apparatus 81 comprises a conventional output display, monitor and suitable power source.

A second end of the electrical conduit 55 comprises a contact/connector for external apparatus such as an EEG device, where the tail comprises a cable assembly 56. The contacts on the cable assembly 56 engage the EEG cable assembly connecting block 62, where the block engages connecting wires 63 (which includes male EEG input pin jack 64) of the EEG cable assembly via connecting pins 61. Further, said input pin jack 64 electrically connects to a conventional EEG, where said EEG comprises a conventional output display, monitor and suitable power source.

At least one of the connecting wires 63 of the EEG cable assembly electrically connects to a DC amplifier 96 at electrical connection 98. A platinum needle electrode 58 also electrically connects to the DC amplifier 96. Said DC amplifier 96 comprises a conventional output display, monitor and suitable power source. Moreover, at least one of the connecting wires 63 of the EEG cable assembly electrically may connect to a separate external apparatus 100, wherein apparatus 100 comprises a conventional output display, monitor and suitable power source.

Such a set up allows for real-time monitoring of electrophysiological responses of the brain during pre- and post-operative procedures.

Figure 8A:
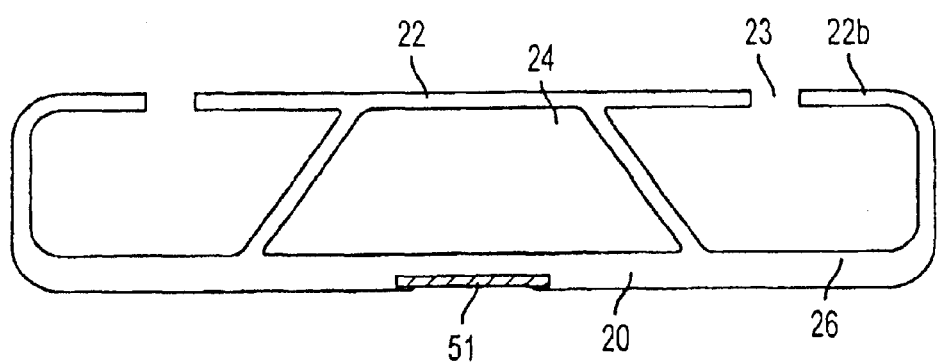
FIG. 8A Cross-sectional view of SS at point A in FIG. 7.

In FIG. 8A, a cross-sectional view of the SS 11 is illustrated from the perspective from point A of FIG. 7.

A detailed view of the fluid-filled (expanded) bladder/cavity 24 is shown in FIG. 8A, including the roof 22 and the bladder/cavity 24 of the elastomer grid 20. Further, a partially exposed electrode 51 which makes contact with the tissue (i.e., the brain) is also shown.

The contours of the perforated drain comprising the grid 11 is also shown in the cross-sectional view of FIG. 8A, such is represented by the opening on the outer surface of grid 11 at 23 (to include the roof of said drain at 22b), where 23 allows evacuation of residual fluid into the lumen 26.

Figure 8B:
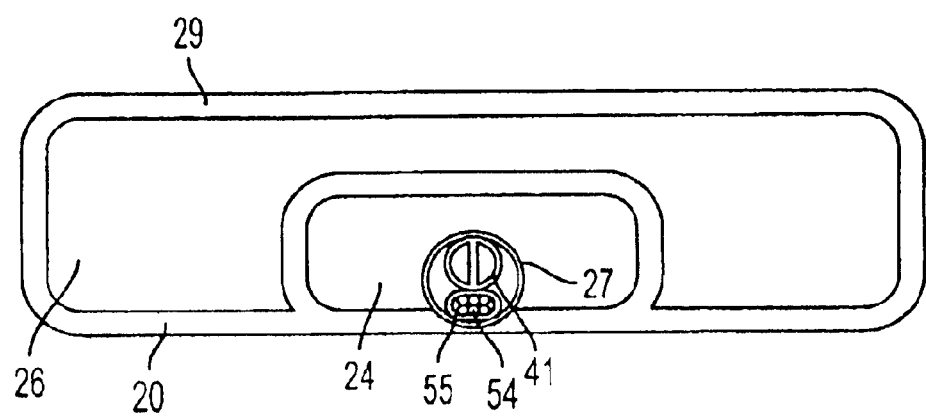
FIG. 8B Cross-sectional view of SS at point B in FIG. 7.

In FIG. 8B, the cross-sectional view of the SS 12 11 is illustrated from the perspective from point B of FIG. 7.

A detailed view of the fluid-filled (expanded) bladder/cavity 24 is shown in FIG. 8B, including the sheathing conduit 29, bladder/cavity 24, which has tapered here from its more distal width, and drain lumen 26 of the elastomer grid 20. Further, a cross-section of conduit 27, which sheathes the hydraulic double lumen catheter 41 and electrical conduit 55 is also shown.

Cross-sectional detail of the sheathing-conduit 27 illustrates the inner lumenal surfaces of the double lumen catheter 41 and the electrical conduit 55, including the coated wire leads 54. The lumens each serve separate purposes; i.e., one lumen is for the evacuation of gases such that there are no air bubbles present in the conduit and cavity/bladder, and the other lumen to measure/monitor pressure.

Figure 8C:
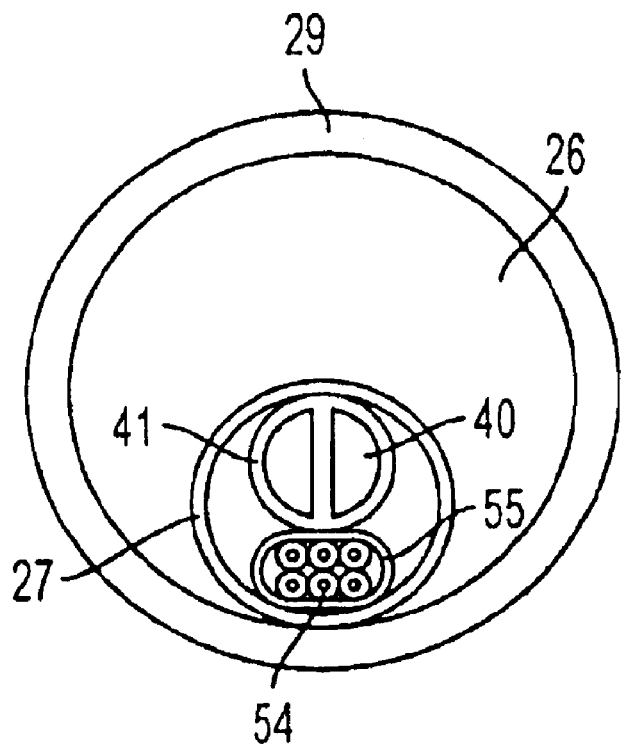
FIG. 8C Cross-sectional view of SS exiting conduit at point C in FIG. 7.

In FIG. 8C, the cross-sectional view of the SS 11 is illustrated from the perspective from point C of FIG. 7.

A detailed view of the sheathing conduit 29, comprising drain lumen 26 and conduit 27. Further, a cross-section of conduit 27, which sheathes the hydraulic double lumen catheter 41 and electrical conduit 55 is also shown.

Cross-sectional detail of the sheathing-conduit 27 illustrates the inner lumenal surfaces of the double lumen catheter 41 and the electrical conduit 55, including separate, coated wire leads 54. The lumens (40) each serve separate purposes; i.e., one lumen is for the evacuation of gases such that there are no air bubbles present in the conduit and cavity/bladder and the other lumen to measure/monitor pressure.

Figure 9A:
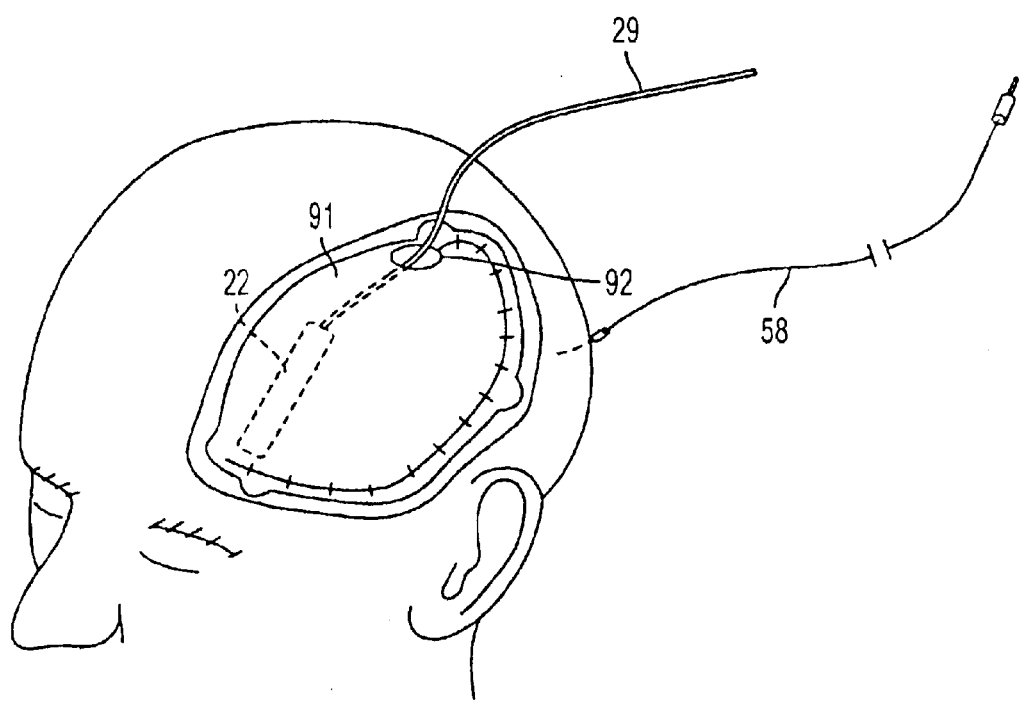
FIG. 9A Perspective view of subdural placement of intracranial sensor for either stage I of epilepsy surgery or for surgery for head trauma. Scalp flap and removed bone flap are not shown.

FIG. 9A is a perspective view of an intracranial sensor placed subdurally (e.g., SS 11) for surgery, where the scalp and bone flaps are not shown. The figure shows the roof of the cavity/bladder 22, the dura mater 91 and the opening of dura mater 92 permitting exit of the sheathing conduit 29 and the a platinum needle reference electrode 58.

Figure 9B:
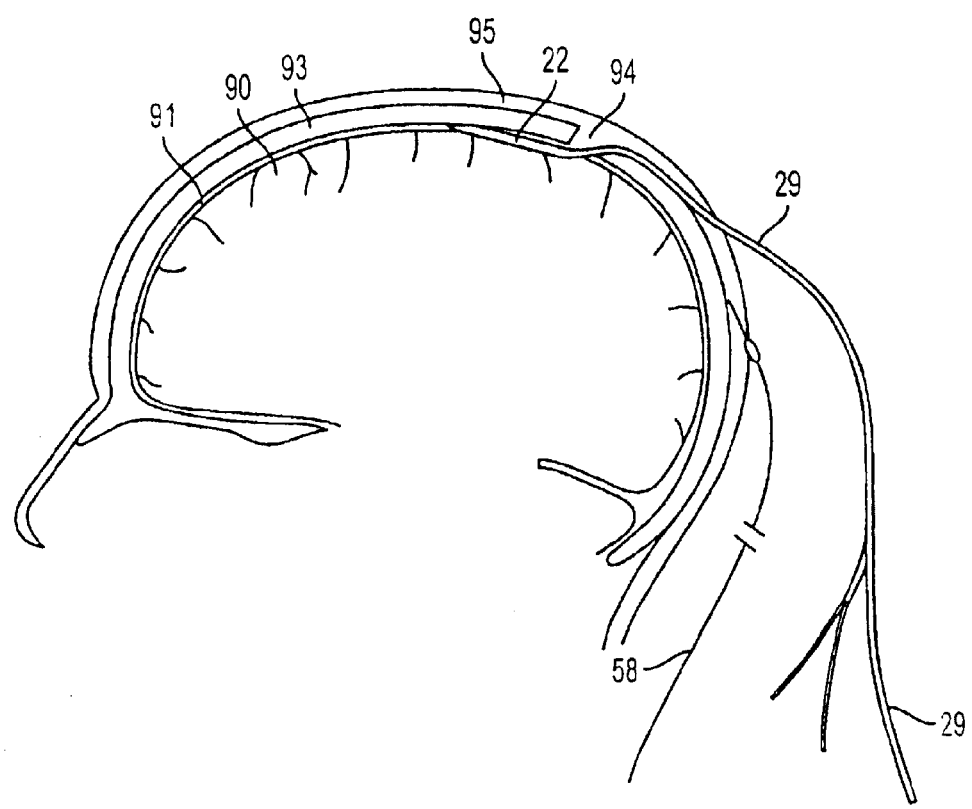
FIG. 9B Sagittal section view of intracranial sensor placed subdurally, as in FIG. 7A. Pt needle reference electrode also shown. Exit of conduit is via a burr hole in calvarium.

FIG. 9B is a sagittal view of an intracranial sensor placed subdurally (e.g, SS 11). The figure shows the roof of the cavity/bladder 22, the dura mater 91, cerebral tissue 90, the calvarium 93, the scalp 95 and a burr hole in the calvarium permitting exit of conduit 29.

While this invention has been described in connection with various embodiments, alternative physical configurations of the devices are envisaged by the present invention.

The following example is included for purposes of illustrating certain aspects of the invention and should not be construed as limiting.

EXAMPLES

Example I

A series of experiments was carried out in anesthetized New Zealand white rabbits in order to evaluate the function of the BRS. Rabbits were placed in a stereotactic head frame, and a temporo-parietal craniotomy was performed using a high-speed surgical drill. Using a retractor blade with BRS mounted to a micromanipulator, groups of animals underwent medially-directed retraction of the lateral temporal lobe at an initial pressure of 20, 30 or 40 mm Hg, as gauged by the device, for either 15 or 30 min. Electrocorticogram (ECoG), which refers to EEG taken directly from the cortical surface rather than scalp, along with cortical DC potential and retraction pressure were recorded on a Bio-logic digital polysomnographic monitor during the retraction period and for 8 hours post-injury. The latter two modalities were amplified via a battery-powered Iso-Dam® high-input impedance DC amplifier (World Precision Instruments, Sarasota, Fla.) and catheter strain gauge with bridge amplifier (TransBridge, World Precision Instruments, Sarasota, Fla.), respectively. The reference electrode for DC potential was placed in trapezius muscle. At the conclusion of the experiment, the brains were removed, sectioned in 2 mm slices, and stained to permit volumetric quantitation of histopathologic injury.

Figure 10:
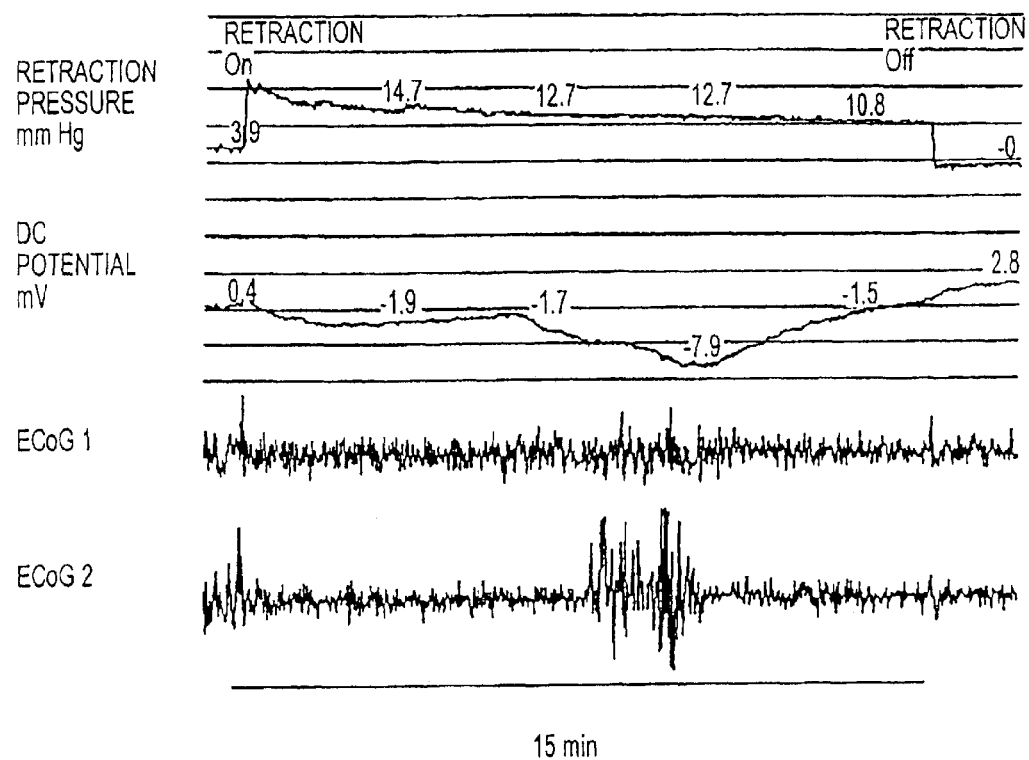
FIG. 10 Digital recording of data obtained from the BRS during medial retraction of the temporal lobe in an experimental rabbit. DC potential and electrocorticograph (EcoG) were recorded from the distal most platinum contact.

FIG. 10 illustrates the recorded data during retraction from a typical experiment where the temporal lobe was retracted to an initial pressure of 20 mm Hg for 15 minutes. Prior to retraction, the resting pressure of the blade against the brain was 3.9 mm Hg. The decay of retraction pressure to about 50% of initial pressure seen in this figure is typical, and is believed to be due to local redistribution of blood volume in the cerebral hemisphere secondary to compression. Minutes after the onset of retraction, the negative DC potential shift is apparent from the tracings. Because the degree of retraction in this particular experiment is relatively mild, normalization of the negative DC shift actually starts prior to the conclusion of the retraction period, unlike that seen with more severe retraction. In the ECoG2 channel, recorded from the second most distal contact of the BRS, an epileptiform spike discharge occurs at about the time of the peak of the DC shift. This type of activity is not uncommon during retraction of the temporal lobe in this animal model. This particular animal demonstrated a fairly mild degree of histopathologic injury compared to other rabbits in the study.

Using the sensor, the data from this investigation demonstrates significant regression correlations between retraction pressure (in terms of the pressure-time integral, which takes the decay into account) and both the severity of the negative DC potential shift as well as the volume of histopathologic injury. A similar type of study using the BRS is also being carried out in patients undergoing surgery for aneurysm clipping or resection of skull-base tumors. Rather than by quantitation of histologic damage, in this study injury is assessed in terms of radiographic signal abnormality and presence or absence of clinical deficit referable to retraction postoperatively. This analysis will hopefully permit the establishment of criteria for retraction injury threshold based on retraction pressure-duration and electrocortical parameters. Currently, such guidelines do not exist.

It will be understood that various modifications may be made to the embodiments disclosed herein. Therefore, the above description should not be construed as limiting, but merely as exemplifications of preferred embodiments. Those skilled in the art will envision other modifications within the scope and spirit of the claims appended hereto.

All patents and references cited herein are explicitly incorporated by reference in their entirety.

I claim:

1. A sub-dural sensor device comprising:
    an elongated first end comprising a substantially inextensible cavity, wherein said first end is configured to be placed sub-durally;

a plurality of non-polarizable electrodes exposed along at least one surface of said first end, and an electric conduit and a hydraulic conduit comprising an exit port at a shortened second end, wherein said first end engages said second end at said exit port, and further wherein one end of said electric conduit and one end of a remote reference electrode electrically connect to a differential DC amplifier.

2. The device of claim 1, wherein said first end comprises substantially flat, smooth atraumatic faces.

3. The device of claim 1, wherein said first end comprises a thin, elastically deformable, bio-compatible material that conforms to contours of the brain.

4. The device of claim 1, wherein said electric conduit comprises at least one tail at an end distal to said first end, wherein said at least one tail allows for communications between the device and at least one peripheral apparatus.

5. The device of claim 1, wherein said cavity comprises a bladder or a network of interconnected lumens internal to a flat matrix.

6. The device of claim 1, wherein said hydraulic conduit comprises a flexible, noncompliant material having at least two lumenal surfaces.

7. The device of claim 6, wherein said hydraulic conduit comprises a double lumen catheter.

8. The device of claim 7, wherein one end of each separate lumeral surface comprising said double lumen catheter engages separate fluid-flow directing connectors.

9. The device of claim 8, wherein said fluid flow connectors are female luer-lock connectors.

10. The device of claim 9, wherein said connectors are affixed in a single unit.

11. The device of claim 1, wherein said cavity comprises a fluid selected from the group consisting of normal saline, buffered salt solution, Ringer's solution, Elliott's B solution, and mock cerebrospinal fluid.

12. The device of claim 1, wherein said first end can accommodate pressures of between about one mm Hg and about 120 mm Hg.

13. The device of claim 1, wherein the outer surface flanking the cavity of said elongated first end further comprises a plurality of perforations, wherein said perforations allow liquids to flow into a cistern or lumenal surface below said outer surface for the collection of residual fluids.

14. The device of claim 13, wherein said cistern or lumenal surface channels said residual fluids to one end of said elongated first end, wherein said cistern or lumenal surface engages a conduit, and further wherein said conduit engages an apparatus for collecting said fluid.

15. The device of claim 13, wherein said residual fluids are serosanguineous wound fluid or cerebral spinal fluid (CSF).

16. The device of claim 14, wherein said residual fluid flows into said apparatus by gravity flow.

17. The device of claim 14, wherein said apparatus is a bag.

18. The method of measuring intracranial pressure and cortical electrical activity comprising:

situating at least one device of claim 1 underneath the dura mater of the brain through at least one burr hole in the calvarium;

contacting said device on the surface of a brain; and recording intracranial pressure and cortical DC potential and/or EEG.

19. The method of claim 18, wherein said measuring comprises application of said at least one device to a patient with intractable epilepsy, wherein placement of the device localizes focal seizures identified by EEG monitoring.

20. The method of claim 19, wherein said placement of the device allows for concurrent monitoring of intracranial pressure (ICP) and prompt administration of medicaments when ICP reaches critical values.

21. The method of claim 19, wherein said critical ICP is between about 20 and about 30 mm Hg.

22. The method of claim 19, wherein said measuring comprises application of said at least one device to a patient with severe closed head injury, wherein placement of the device is at the surface of the brain to permit assessment of swelling postoperatively.

23. A brain retractor sensor (BRS) device comprising:

an elongated first end comprising a substantially inextensible cavity; a plurality of non-polarizable electrodes exposed along a front face of said first end;

at least one releasable coupling projection comprising a back face of said first end;

and an electric conduit and a hydraulic conduit comprising an exit port at a shortened second end, wherein said first end engages said second end at said exit port, and further wherein one end of said electric conduit and one end of a remote reference electrode electrically connect to a differential DC amplifier.

24. The device of claim 23, wherein said first end comprises substantially flat, smooth atraumatic faces.

25. The device of claim 23, wherein said first end comprises a thin, elastically deformable, bio-compatible material that conforms to shaped angles of a retractor blade.

26. The device of claim 23, wherein said electric conduit further comprises at least one tail at an end distal to said first end, wherein said at least one tail allows for communication between the device and at least one peripheral apparatus.

27. The device of claim 23, wherein said projection is selected from the group consisting of a sleeve and a pocket.

28. The device of claim 25, wherein said cavity comprises a bladder or a network of interconnected lumens internal to a flat matrix.

29. The device of claim 25, wherein said bio-compatible material is selected from a group consisting of silicone-based materials, thermoplastic elastomer, low density polyethylene, and polyurethane.

30. The device of claim 23, wherein said hydraulic conduit comprises a flexible, noncompliant material having at least two lumenal surfaces.

31. The device of claim 30, wherein said hydraulic conduit comprises a double lumen catheter.

32. The device of claim 31, wherein one end of each separate luminal surface comprising said double lumen catheter engages separate fluid-flow directing connectors.

33. The device of claim 32, wherein said fluid flow connectors are female luer-lock connectors.

34. The device of claim 33, wherein said connectors are affixed in a single unit.

35. The device of claim 23, wherein said cavity comprises a fluid selected from the group consisting of normal saline, buffered salt solution, Ringer's solution, Elliott's B solution, and mock cerebrospinal fluid.

36. The device of claim 23, wherein said cavity can accommodate pressures of between about one mm Hg and about 120 mm Hg.

37. A method of averting brain injury during neurosurgical retraction comprising:

a) situating the BRS of claim 23 between the brain and a retractor blade;

b) supplying a physiologically inert fluid throughout said elongated end;

c) recording retraction pressure and cortical electrical activity; and d) communicating to a surgeon performing said retraction abnormal recordings from step (c), wherein said surgeon adjusts retractor position to avoid brain injury based on said abnormal recordings.

38. The method of claim 37, wherein said situating of the BRS comprises releasably coupling said BRS to said retractor blade.

39. The method of claim 38, wherein said releasably coupling comprises contacting said blade with a projection from a back surface of said BRS.

40. The method of claim 39, wherein said projection is selected from the group consisting of a sleeve and a pocket.

41. The method of claim 37, wherein said non-polarizable electrodes are selected from the group consisting of platinum and Ag—AgCl.

42. The method of claim 37, wherein said physiologically inert fluid is selected from the group consisting of normal saline, buffered salt solution, Ringer's solution, Elliott's B solution, and mock cerebrospinal fluid.

43. The method of claim 37, wherein said recording in step (c) comprises referencing cortical DC potential at a remote site via a needle electrode.

* * * * *